(12) United States Patent
Briand et al.

(10) Patent No.: US 7,820,176 B2
(45) Date of Patent: Oct. 26, 2010

(54) ULVANS AS ACTIVATORS OF PLANT DEFENSE AND RESISTANCE REACTIONS AGAINST BIOTIC OR ABIOTIC STRESSES

(75) Inventors: Xavier Briand, Lezardrieux (FR); Stéphanie Cluzet, Toulouse (FR); Bernard Dumas, Montrabe (FR); Marie-Thérèse Esquerre-Tugaye, Castanet-Tolosan (FR); Sylvie Salamagne, Gressy en France (FR)

(73) Assignee: TIMAC Agro International, Saint Malo (FR)

( * ) Notice: Subject to any disclaimer, the term of this patent is extended or adjusted under 35 U.S.C. 154(b) by 43 days.

(21) Appl. No.: 10/594,692

(22) PCT Filed: Mar. 30, 2005

(86) PCT No.: PCT/FR2005/000765

§ 371 (c)(1), (2), (4) Date: May 31, 2007

(87) PCT Pub. No.: WO2005/094588

PCT Pub. Date: Oct. 13, 2005

(65) Prior Publication Data

US 2007/0232494 A1 Oct. 4, 2007

(30) Foreign Application Priority Data

Mar. 30, 2004 (FR) .................................. 04 03269

(51) Int. Cl.
*A61K 36/02* (2006.01)
(52) U.S. Cl. ................................. 424/195.17
(58) Field of Classification Search ........................ None
See application file for complete search history.

(56) References Cited

U.S. PATENT DOCUMENTS

| 5,672,503 | A  | * | 9/1997 | Nairn et al. |
| 6,837,002 | B2 | * | 1/2005 | Costa |
| 2004/0023924 | A1 | * | 2/2004 | Lienart |

FOREIGN PATENT DOCUMENTS

| FR | 2814471 A1 * | 3/2002 |
| WO | WO 91/07946 | 6/1991 |
| WO | WO 99/53761 | 10/1999 |
| WO | WO 02/26037 | 4/2002 |

OTHER PUBLICATIONS

Lahaye, M. et al. Journal of Applied Phycology (1993); 5: 195-200. Chemical and physical-chemical characteristics of dietary fibres from *Ulva lactuca* (L.) Thuret and *Entermorpha compressa* (L.) Grev.*
Sekar, R et al. Phykos (1995), 34(1-2): 49-53. Effect of seaweed liquid fertilizer from *Ulva lactuca* L. on *Vigna unguiculata* L. (Walp.).*
Ahilan, M. et al. Seafood Export J (1990), 22(9-10): 23-25. Seaweed, is it really useful?*
Bi et al., "Studies on Aqueous Extracts of Three Green Algae as an Elicitor of Plant Defence Mechanism" *Pak. J. Bot.* vol. 31 No. 1 pp. 193-198 (1999).
Paradossi et al., "A Conformational Study on the Algal Polysaccharide Ulvan" Macromolecules. vol. 35 pp. 6404-6411 (2002).
Lahaye et al., "Chemical Characteristics of Insoluble Glucans From the Cell Wall of the Marine Green Alga *Ulva lactuca* (L.) Thuret" Carbohydrate Research. vol. 262 pp. 115-125 (1994).

* cited by examiner

*Primary Examiner*—Michele C. Flood
(74) *Attorney, Agent, or Firm*—Hamre, Schumann, Mueller & Larson, P.C.

(57) ABSTRACT

The present invention relates to the use of ulvans, in particular extracted from green algae of the genus *Ulva* or *Enteromorpha*, or of ulvan-derived oligosaccharides, as activators of plant defense and resistance reactions against biotic or abiotic stresses.

It also relates to a plant-protection product containing ulvans and to the uses thereof in a plant treatment method.

14 Claims, No Drawings

ULVANS AS ACTIVATORS OF PLANT DEFENSE AND RESISTANCE REACTIONS AGAINST BIOTIC OR ABIOTIC STRESSES

The present invention, which can be used in the agricultural field, essentially relates to the use of ulvans, in particular extracted from green algae of the genus *Ulva* or *Enteromorpha*, or of ulvan-derived oligosaccharides, as activators of plant defense and resistance reactions against biotic or abiotic stresses.

The present invention also relates to plant-protection products containing these ulvans or ulvan-derived oligosaccharides and also to a method for treating plants, in particular via the leaves or the roots, using them.

These plants can be attacked by many pathogenic agents (fungi, bacteria, viruses, viroids, protozoa, nematodes, herbivores) with resulting losses in yield and a reduction in production quality.

In parallel with chemical control, which resorts to the use of pesticides, new plant protection strategies have come to light.

In fact, although they lack an immune system analogous to higher animals, plants have their own defense arsenal. Knowledge of these mechanisms makes it possible to envision the use thereof for combating diseases.

The control, by the plant, of the effects of the pathogen results from a series of events triggered in the plant cells from the moment the plant is attacked:
1. the pathogenic agent is recognized,
2. this information is sent to the nucleus,
3. defense genes are induced and antimicrobial compounds are then synthesized,
4. the alarm signal is transmitted to the entire plant and to its neighbors.

Thus, in order to increase the response and therefore resistance capacity of a plant with respect to certain pathogens, one of the possible strategies consists in inducing, prior to attack by the pathogen, the defense reactions using signal molecules.

These signal molecules, the chemical nature of which is very varied (proteins, peptides, glycoproteins, lipids and oligosaccharides), are capable of transmitting the information of an attack even at very low concentration.

Most of them are of bacterial origin (for example harpin) or plant origin (for example, oligogalacturonic acids) or are chemically synthesized (for example benzothiadiazole).

In response to treatments with these signal molecules, the plant reacts by synthesizing structural proteins which strengthen the plant cell wall, enzymes involved in the synthesis of antimicrobial compounds, such as phytoalexins, hydrolases such as chitinases or glucanases and inhibitory enzymes which act against the hydrolytic enzymes of the pathogenic agents.

In the case of a plant-parasite interaction of incompatible type, the defense responses most commonly observed are:
 rapid cell death localized at the site of infection, also called hypersensitive response or "HR",
 the synthesis and deposit of phenolic compounds and of proteins in the wall,
 the accumulation of antimicrobial compounds and the synthesis of "PR" (for Pathogenesis-Related) proteins.

The reinforcement of the structural barriers, which can slow down or inhibit the progression of the pathogen into the plant, is often associated with the HR. For example, the deposition of callose in the wall or the plasmodesma and the synthesis of lignins make it possible to slow down fungal or viral invasions. Similarly, extensin HRGPs (for Hydroxyproline Rich GlycoProteins), and GRPs (for Glycine Rich Proteins) can, by virtue of their wall strengthening role, render the latter more difficult to degrade.

Phytoalexins, which are low-molecular-weight antimicrobial compounds, make it possible, in certain cases, to directly combat parasites due to their ability to accumulate rapidly around the point of infection, thus preventing progression of the invasion. More than 350 phytoalexins have been isolated and characterized from about thirty plant families. They exhibit great structural diversity and derive from the secondary metabolisms of shikimate, of acetate-malonate and of acetate-mevalonate. Some are found in several plant families, while others are specific for a given family. This is in particular the case of the isoflavons of leguminous plants or of the sesquiterpenes of Solanaceae. It should, however, be noted that phytoalexins do not appear to play an essential role in the resistance to all pathogenic agents, such as, for example, for *Arabidopsis thaliana*.

The HR is also accompanied by the synthesis of PR proteins. These intracellular or extracellular proteins accumulate in the plants after they have been inoculated with pathogenic agents and, in the case of incompatible interactions, can constitute up to 10% of the soluble proteins of the leaf. For some, an active role in wall degradation by fungal pathogenic agents ($\beta$-glucanase, chitinase) has been shown.

It should be noted that the abovementioned three phenomena (wall strengthening, phytoalexin synthesis and PR protein synthesis) accompany the HR without being exclusive thereto. In fact, the synthesis of GRP and HRGP proteins has also been detected during compatible interactions, and also subsequent to an injury.

Marine algae constitute an abundant plant resource and have, for a long time, been used in coastal regions as soil fertilizers. Seed germination, the production of better yields, resistance to diseases, and a longer storage period for fruit have been demonstrated following treatment of several plants with algal extracts. The conclusions in terms of plant health had essentially been attributed to the richness in betains, plant hormones and trace elements of the algae used.

It is now recognized that certain oligosaccharides of marine origin have an elicitor effect on certain plant defense pathways. Thus, document WO 99/03346 describes the use of $\beta(1-3)$-glucan type oligosaccharides, in particular extracted from the brown alga *Laminaria digitata*, for the potentiation and stimulation of the natural defenses of wheat infected with septorial disease. These $\beta(1-3)$-glucans also induce, in tobacco cells, four defense markers, including phenylammonialyase (PAL) activity, which is a key enzyme for phytoalexin synthesis, and O-methyl transferase (OMT) activity, which is an enzyme involved in lignin synthesis.

In the case of red algae, it has been shown that carrageenan induces the expression of genes encoding sesquiterpene cyclase, chitinase and proteinase inhibitors.

In the case of green algae, which themselves also are rich in polysaccharides, no study has to date demonstrated that polysaccharides extracted from these algae exhibit elicitor properties comparable with those demonstrated in brown and red algae.

It is in this context that it has been discovered, and this constitutes the basis of the present invention, that ulvans, in particular extracted from green algae, and the oligosaccharides derived from the latter make it possible, entirely surprisingly and unexpectedly, to stimulate the expression of plant defense genes and can therefore be used as activators of plant defense and resistance reactions against biotic or abiotic stresses, in particular as a replacement for pesticides and as a supplement in fertilizing compositions or in fertilizers.

Thus, according to a first aspect, the present application aims to cover the use of ulvans, in particular extracted from green algae of the genus *Ulva* or *Enteromorpha*, or of ulvan-derived oligosaccharides, as activators of plant defense and resistance reactions against biotic or abiotic stresses.

The ulvans which can be used according to the invention are water-soluble polysaccharides present in particular in the cell walls of green algae of the genera *Ulva* and *Enteromorpha*.

The ulvans are defined more specifically as highly sulfated acidic polysaccharides and are essentially composed of units derived from rhamnose 3-sulfate, from xylose, from xylose 2-sulfate, from glucuronic acid and from iduronic acid.

The following four repeating units are in particular characteristic of ulvans:

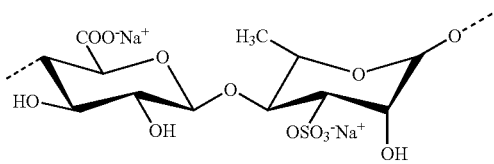

>4)-β-D-GlcA-(1>4)-α-L-Rha 3 sulfate(1> (also called ulvanobiouronic acid 3-sulfate type A)

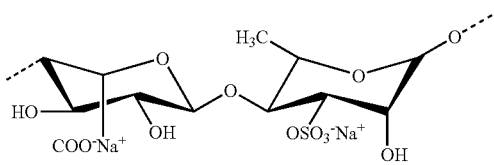

>4)-α-L-IdoA-(1>4)-α-L-Rha 3 sulfate(1> (also called ulvanobiuronic acid 3-sulfate type B)

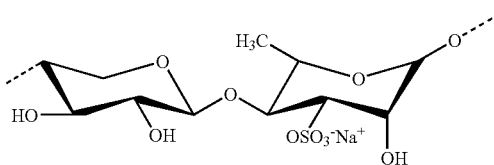

>4)-β-D-Xyl-(1>4)-α-L-Rha 3 sulfate(1> (also called ulvanobiose acid 3-sulfate)

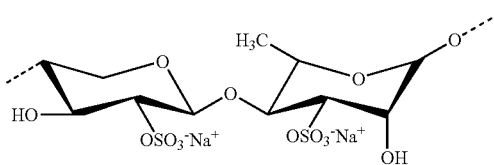

>4)-β-D-Xyl 2-sulfate-(1>4)-α-L-Rha 3 sulfate(1> (also called ulvanobiose acid 2',3-disulfate)

Ulvans represent between 5 and 20% of the dry weight of the alga. Their molecular weight ranges between 90 000 and 500 000 g.mol$^{-1}$ in the genera *Ulva* and *Enteromorpha*.

Advantageously, the ulvans used according to the present invention are extracted from algae chosen from the group consisting of the following species: *Ulva armoricana, Ulva rigida, Ulva rotundata, Ulva lactuca, Enteromorpha intestinalis* and *Entoromorpha compressa*.

Extracts of algae rich in ulvans which can be used in the context of the present invention can be obtained from the abovementioned algae species, by means of a method generally comprising the following steps: washing, milling, extraction (solid-liquid separation) and, optionally, fractionation and concentration.

The extract obtained can be more or less concentrated according to the use envisioned. Complete dehydration of this extract, allowing it to be provided in a water-soluble pulverulent form, can be obtained, for example, by drying in a drum or by spraying.

The ulvan-derived oligosaccharides which can be used in the context of the invention can be obtained by acid hydrolysis or enzymatic hydrolysis using the abovementioned extracts.

The extraction conditions and the nature of the algae will be chosen such that the extract obtained has the concentration desired in the application envisioned. These choices may be readily made by those skilled in the art, in particular by taking into account the general indications which will follow.

In general, the amount of ulvans or of ulvan-derived oligosaccharides given to the plants is from 0.1 g to 100 g per liter, and preferably of the order of 1 g per liter, when applied in liquid form via the leaves or in nutritive solutions for the roots (hydroponics, dropwise, etc.) or else from 10 to 1000 g/ha, and preferably of the order of 200 g/ha, when applied in solid form in pulverulent or granulated fertilizers.

The amount of ulvans given to the plants must be sufficient to stimulate the expression of the genes involved in plant defense. This amount is variable according to the nature of the plant to be treated and the method of treatment (administration via the leaves or via the roots). This amount may in particular be determined case by case by carrying out macroarray tests as defined below.

According to a second aspect, the present application aims to protect a plant treatment method intended to activate defense and resistance reactions against biotic or abiotic stresses, characterized in that it comprises the application, to said plants, of an effective amount of ulvans, in particular extracted from green algae of the genus *Ulva* or *Enteromorpha*, or of ulvan-derived oligosaccharides.

Advantageously, the application to the plants will be carried out via the leaves or via the roots.

The effective amount of ulvans or of ulvan-derived oligosaccharides given to the plants is from 0.1 g to 100 g per liter, and preferably of the order of 1 g per liter, when applied in liquid form via the leaves or in nutritive solutions for the roots (hydroponics, dropwise, etc.), or else from 10 to 1000 g/ha, and preferably of the order of 200 g/ha, when applied in solid form in pulverulent or granulated fertilizers.

Finally, according to a third aspect, the present application aims to protect a novel plant-protection product, characterized in that it comprises an effective amount of at least one ulvan, in particular extracted from green algae of the genus *Ulva* or *Enteromorpha*, or an ulvan-derived oligosaccharide, optionally in combination with one or more fertilizing substances.

This plant-protection product will advantageously be in the form of a liquid or in the form of a powder or granule, it being possible for the latter soluble forms to be diluted with an appropriate amount of solvents, such as, for example, water.

This product will advantageously contain an effective amount of ulvans or of ulvan-derived oligosaccharides given to the plants, of from 0.1 g to 100 g per liter, and preferably of the order of 1 g per liter, when applied in liquid form via the leaves or in solutions for the roots (hydroponics, dropwise, etc.), or else from 10 to 1000 g/ha, and preferably of the order of 200 g/ha, when applied in solid form.

By way of examples of fertilizing products in accordance with the invention, mention will be made of calcareous enriching agents, organic enriching agents and crop supports, root fertilizers of the type NP, PK, NPK, etc., leaf fertilizers or nutritive solutions for the roots.

The fertilizing substances which can be used in combination with the ulvans or the ulvan-derived oligosaccharides may be varied in nature and may be chosen, for example, from urea, ammonium sulfate, natural phosphate, potassium chloride, ammonium sulfate, magnesium nitrate, manganese nitrate, zinc nitrate, copper nitrate, phosphoric acid and boric acid.

The present invention can also be used in the treatment of a very large variety of plants.

Among the latter, mention will be in particular be made of:

large crop plants such as cereals (wheat, maize), protein-yielding plants (pea), oil-yielding plants (soybean, sunflower), prairial plants used for animal feed, specialized crops such as, in particular, crops for market gardening (lettuce, spinach, tomato, melon), grapevine, tree cultivation (pear, apple, nectarine), or horticulture (rose bushes).

The expression "plant" is intended to denote, in the present application, the plant considered as a whole, including its root system, its vegetative system, the grains, seeds and fruits.

The present invention will now be illustrated by means of the following nonlimiting examples.

In these examples, and unless otherwise indicated, the percentages are expressed by weight and the temperature is ambient temperature.

EXAMPLE 1

Method for Preparing an Ulvan-Rich Alga Extract which can be Used in the Context of the Invention A—General Description a) Preparation of Ulvans The ulvan fraction is obtained by aqueous extraction of fresh algae (100 g of fresh algae per liter of water).

The extraction is carried out with stirring at 90° C. for 2 hours. The extract is then filtered through a membrane (80 μm porosity). The solvent (water) is evaporated off so as to obtain a water-soluble powder.

b) Preparation of Oligoulvans

The ulvans prepared as indicated in a) above are hydrolyzed in 1 liter of acid solution (trichloroacetic acid or hydrochloric acid concentrated at 2-3 mol L$^{-1}$) at 100° C. for 30 min to 1 h, preferably of the order of 40 min.

Glucuronic acid, aldobiuronic acid, ulvanobiouronate and iduronic acid were identified in the hydrolysis products.

B. Detailed Example of Extraction:

An extract of *Ulva armoricana* enriched in ulvans, and in particular in derivatives of iduronic acid of xyloidurorhamnan type, was obtained according to the following experimental protocol:

a) Washing

Fresh algae of *Ulva armoricana* type are subjected to two successive washes in a tank of water, in order to remove the sand and gravel.

The algae are then placed in stainless steel wire mesh baskets before being introduced into tanks where they are covered with water.

Agitation by means of aeration nozzles makes it possible to maintain the algae in suspension, thus promoting the settling out of impurities.

b) Milling

The algae thus washed are drained and then milled into pieces of 1 to 10 mm.

c) Extraction 1000 kg of algae are dispersed in a heating reactor containing 10 000 kg of an aqueous solution brought to a temperature of 90° C. The whole is kept at this temperature for a period of approximately 2 hours.

Prior to the extraction, the algal cells already milled are micro-ruptured by means of an ULTRA-TURAX® homogenizer in order to promote extraction. The separating process occurs after 2 hours of extraction.

d) Separation

The soluble fraction rich in iduronic acid derivatives of xyloidurorhamnan type is separated from the algal debris by centrifugation (solid-liquid separation).

The centrifuged extract is then filtered, either through a diatomaceous earth filter, or through a plate filter, and then again filtered through a membrane of up to 1 μm.

The filtrate thus obtained contains between 0.1 and 1% by weight of dry extract.

The extract thus prepared can be used in a more or less concentrated form, the final concentration being determined according to the desired content of derivatives that are active in the application envisioned.

Thus, the filtrate mentioned above can be concentrated, for example by means of a falling-film evaporator, such that the dry extract represents from 10 to 60% by weight of said filtrate.

Complete dehydration can also be obtained, for example, with a drum dryer or by spraying, when a presentation in water-soluble pulverulent form is desired.

By proceeding as described above, various extracts were prepared from six species of green algae of the genus *Ulva* or *Enteromorpha*. The composition of these dry extracts is given in Table 1 below.

TABLE 1

Composition of the extracts of green algae

| Alga | % of ulvans (% of the dry weight of the alga) | % of total sugars | % of sulfate | % of proteins |
|---|---|---|---|---|
| Ulva armoricana | 7-15 | 50-80 | 10-20 | 3-7 |
| Ulva rigida | 5-18 | 50-80 | 13-17 | 1-10 |
| Ulva rotundata | 6-15 | 50-70 | 10-20 | 1-10 |
| Ulva lactuca | 5-17 | 50-70 | 10-20 | 1-8 |
| Enteromorpha intestinalis | 5-15 | 45-75 | 15-20 | 1-10 |
| Enteromorpha compressa | 5-16 | 50-75 | 10-20 | 1-12 |

| Alga | Rha | Gal | Glc | Xyl | GlcA | IdoA |
|---|---|---|---|---|---|---|
| Ulva armoricana | 45-50 | 1-4 | 5-20 | 6-15 | 15-25 | 5-15 |
| Ulva rigida | 50-60 | 0.5-2 | 5-8 | 5-15 | 18-35 | 2-5 |

TABLE 1-continued

Composition of the extracts of green algae

| | | | | | | |
|---|---|---|---|---|---|---|
| Ulva rotundata | 45-55 | 1-3 | 5-15 | 5-25 | 16-30 | 0.5-5 |
| Ulva lactuca | 45-60 | 0.5-5 | 2-6 | 1-10 | 15-25 | 2-5 |
| Enteromorpha compressa | 25-50 | 1-5 | 2-10 | 5-15 | 10-20 | 5-10 |
| Enteromorpha intestinalis | 30-50 | 1-4 | 1-5 | 6-15 | 15-20 | 5-10 |

EXAMPLE 2

A—Demonstration of the Effects of the Ulvans on the Expression of the Genes of a Model Plant An overall analysis of the expression of numerous genes involved in the defense of a model plant was carried out using functional genomic techniques. The leguminous plant *Medicago truncatula* (large number of available DNA sequences) was used as model plant.

The effect of the ulvans was thus studied on approximately 200 genes involved in the defense of this model plant, by macroarray analysis.

a) Biological Material

*Medicago truncatula* line F83 005.5 plants were cultivated in a controlled environment (16 h/8 h, 20° C./15° C., 60% humidity).

The products studied (extracts obtained according to the method of Example 1) were applied via the leaves or via the roots.

In the case of application via the leaves, the various solutions of elicitors are sprayed onto the leaves of the 1-month-old plants at the concentration of 1 mg/ml.

In the case of application via the roots, the products are introduced into the nutritive medium.

The study of the overall expression of the genes potentially involved in defense and in signaling was pursued by macroarray.

b) Preparation of the Macroarrays

A selection of expressed gene tags (ESTs) of *Medicago truncatula*, based essentially on their involvement in plant defense and in primary metabolism, was carried out using the TGIR and MENS databases.

165 ESTs belonging to 144 sequences of *Medicago truncatula* (tentative consensus sequences (TCs)) are recovered from the MtBA, MtBB and MtBC libraries.

8 genomic fragments (TC76726, TC77277, TC77910, TC77988, TC78214, TC85619, TC86687, TC85808) are amplified by PCR using the *Medicago truncatula* genomic DNA as primer. These 8 ESTs are then cloned into the pGEM-Teasy vector (Promega) and verified by sequencing.

The 173 DNA fragments are amplified by PCR using the universal primers complementary to the vector sequences bordering the DNA cloning site. The amplification products are analyzed by electrophoresis and are adjusted to 0.2-0.5 μg/l with DMSO (50%) and deposited on a membrane by means of a robot (Eurogridder spotting robot).

c) Results

The elicitor activity of the ulvans extracted from algae was studied by simultaneously following the expression of several hundred genes. The various categories of ESTs selected are classified per family: phenylpropanoid pathway, phytoalexin biosynthesis, wall proteins, cell defense, oxidative stress, senescence-HR, ethylene pathway, lipid synthesis, abiotic stress, signal transduction, nodulins, housekeeping genes.

The extracts of green algae rich in ulvans bring about the induction of 16 to 31 genes potentially involved in the defense without disturbing the primary metabolism. Similar responses are obtained for the 2 types of application, i.e. by the leaves and by the roots. For all the treatments, the induction of genes relating to the wall protein, phytoalexin biosynthesis and cell defense families is thus essentially noted.

The gene induction is greater for the ulvans rich in xyloidurorhamnan acid derivatives, such as, for example, the ulvans of *Ulva armoricana* and of *Enteromorpha intestinalis*. The latter also have the particularity of inducing a gene involved in the oxylipin pathway. The oligoulvans obtained after hydrolysis show identical results.

TABLE 2

Effects of the ulvans of various green algae on the expression of certain genes in macroarrays

| | | Ulva | | | | | Enteromorpha | |
|---|---|---|---|---|---|---|---|---|
| | | U. armoricana[2] | | | | | | |
| Gene family | Number of TC[1] | Ulvans | Oligoulvans | U. rigida | U. rotundata | U. lactuca | E. compressa | E. intestinalis |
| Phenylpropanoid pathway | 8 | 4 | 4 | 3 | 3 | 2 | 3 | 4 |
| Phytoalexin pathway | 10 | 5 | 5 | 3 | 2 | 2 | 4 | 5 |
| Wall proteins | 17 | 6 | 5 | 4 | 5 | 3 | 3 | 6 |
| Oxidative stress | 8 | 2 | 2 | 2 | 2 | 1 | 2 | 1 |
| Cell defense | 20 | 5 | 5 | 5 | 4 | 3 | 3 | 5 |
| Senescence-HR | 3 | 1 | 1 | 1 | 1 | 1 | 1 | 1 |
| Ethylene production | 2 | 0 | 0 | 0 | 0 | 0 | 0 | 0 |
| Oxylipin pathway | 23 | 2 | 2 | 0 | 0 | 0 | 0 | 1 |
| Abiotic stress | 3 | 1 | 1 | 1 | 1 | 1 | 1 | 1 |
| Signal transduction | 8 | 4 | 3 | 4 | 4 | 3 | 3 | 4 |
| Nodulins | 6 | 0 | 0 | 0 | 0 | 0 | 0 | 0 |
| Others | 8 | 1 | 1 | 0 | 1 | 0 | 0 | 1 |
| Total | 116 | 31 | 29 | 23 | 23 | 16 | 20 | 29 |

[1]The values correspond to the number of TCs (TIGRs Tentative Consensus Sequences) in each gene family.
[2]The values are means of 3 independent treatments corresponding to the number of genes induced. Only the genes induced twice consecutively (ratios 1.5) are included.

d) Influence of the Number of Treatments on the Sensitization of the Plant

A second series of experiments was carried out in order to evaluate the effect of the sensitization of the plant treated with the extract of *Ulva armoricana*, during the fungal attack. The effect of a second treatment with the extract of *Ulva armoricana,* 3 days after the first spraying, was thus evaluated. The effects on the gene expression are studied by macroarray.

The treatments carried out in one or two applications induce the expression of a large number of genes involved in the defense and signaling mechanisms to a similar degree.

The treatments induce the expression of genes in all the functional categories:
  that of phenylpropanoids: phenylalanine ammonia lyase, caffeic acid O-methyltransferase, cinnamyl alcohol dehydrogenase,
  that of phytoalexins: chalcone reductase, isoflavone reductase, vestitone reductase,
  that of the wall proteins: extensin, hydroxyproline-rich glycoprotein, arabinogalactan-rich protein, proline-rich protein, prolyl hydroxylase endo, endo-1,3-1,4-β-D-glucanase,
  that of the defense genes: PR10-1, endochitinase, SRG1, polygalacturonase inhibitor, PR1.

In the case of oxidative stress, the induction of the expression of various genes encoding various enzymes: ascorbate peroxidase, peroxidase, superoxide dismutase, gluthatione peroxidase or glutathione S-transferase is observed.

In terms of lipid metabolism, various genes involved in the oxylipin pathway are induced, in particular the phospholipases D and C, three lipoxygenases, a desaturase and an oxophytodienoate reductase. Two consecutive treatments induce the expression of a larger number of genes (6 genes versus 2).

TABLE 3

Effects of the ulvans of *Ulva armoricana* (AV) on the expression of certain genes in macroarrays

| | | | Treatment[a] | | | | | |
|---|---|---|---|---|---|---|---|---|
| | | Accession in | AV[d] | | | AV + AV[e] | | |
| TC TIGR[b] | Function | GB[c] | 1 | 2 | 3 | 1 | 2 | 3 |
| Phenylpropanoid pathway | | | | | | | | |
| TC85501 | phenylalanine ammonia lyase | AL372483 | NS | 2.33 | 1.83 | 1.18 | 4.44 | 1.00 |
| TC85550 | caffeic acid O-methyltransferase | AL367074 | 1.52 | 1.93 | 2.54 | NS | 4.33 | 1.90 |
| TC85894 | caffeoyl-CoA O-methyltransferase | AL368189 | 2.03 | 0.67 | 1.57 | NS | 1.22 | NS |
| TC77145 | cinnamyl-alcohol dehydrogenase | AL372163 | 1.00 | 5.47 | 4.33 | 1.03 | 3.40 | 2.01 |
| Phytoalexin pathway | | | | | | | | |
| TC76884 | chalcone synthase | AL369218 | 1.20 | NS | 1.45 | 4.92 | 0.96 | 4.01 |
| TC85146 | chalcone synthase | AL368203 | 1.00 | 2.09 | 2.34 | 2.00 | NS | 1.13 |
| TC85169 | chalcone synthase | AL370220, AL385833 | 1.51 | 2.93 | 1.54 | 2.17 | 0.97 | 2.42 |
| TC85521 | chalcone reductase | AL381630 | 1.00 | 1.00 | NS | 1.85 | 1.00 | 2.95 |
| TC85633 | chalcone isomerase | AL381790 | 2.01 | 3.31 | 1.25 | 4.88 | 6.04 | 5.17 |
| TC85477 | isoflavone reductase | AL384237 | 1.68 | 3.61 | 2.55 | 3.41 | 2.25 | 5.99 |
| TC85478 | isoflavone reductase | AL383870 | 1.00 | 1.00 | NS | 1.99 | 2.09 | 1.00 |
| TC77308 | vestitone reductase | AL383703, AL384920 | 3.96 | 1.92 | 3.09 | NS | 1.00 | 1.00 |
| Wall proteins | | | | | | | | |
| TC76311 | extensin | AL381854 | 1.00 | 2.76 | 1.79 | 2.00 | 2.34 | 1.47 |
| TC76716 | extensin | AL373614 | 1.15 | 3.08 | 2.59 | 1.64 | 3.51 | 2.12 |
| TC77527 | hydroxyproline-rich glycoprotein | AL370995 | 0.77 | 1.19 | NS | NS | 2.50 | 1.56 |
| TC79404 | arabinogalactan-rich protein | AL368602 | 1.00 | 2.08 | 5.16 | 3.33 | 3.37 | 2.97 |
| TC86688 | arabinogalactan-rich protein | AL381434 | 1.00 | 1.94 | 4.04 | 0.75 | NS | 0.74 |
| TC85413 | proline-rich protein | AL386974 | 3.97 | 1.29 | 2.99 | NS | 1.60 | 2.59 |
| TC86651 | prolyl hydroxylase | AL367499 | 1.00 | 1.00 | 3.30 | 1.69 | 2.50 | 1.00 |
| TC86689 | endo-1,3-1,4-β-D-glucanase | AL387547 | 1.62 | 1.89 | 2.09 | 1.19 | 2.51 | 2.00 |
| Defense | | | | | | | | |
| TC76511 | PR10-1 | AL382676 | 1.72 | 5.69 | 4.40 | 3.43 | 1.54 | 2.15 |
| TC76513 | PR10-1 | AL373773 | 2.14 | 12.14 | 2.69 | 3.29 | 3.04 | 1.18 |
| — | PR10-1 | Y08641 | 5.12 | 19.05 | 0.99 | 11.22 | 2.07 | 2.70 |
| TC76833 | endochitinase | AL380364 | 1.16 | 2.19 | 2.61 | 1.52 | 2.22 | 1.43 |
| TC85427 | chitinase | AL388544 | 1.34 | 0.75 | NS | 0.50 | NS | 0.45 |

TABLE 3-continued

Effects of the ulvans of *Ulva armoricana* (AV) on the expression of certain genes in macroarrays

| TC TIGR[b] | Function | Accession in GB[c] | AV[d] 1 | AV[d] 2 | AV[d] 3 | AV + AV[e] 1 | AV + AV[e] 2 | AV + AV[e] 3 |
|---|---|---|---|---|---|---|---|---|
| TC85652 | SRG1 | AL379718 | 1.41 | 1.40 | NS | 1.71 | 3.50 | 1.48 |
| TC85805 | polygalacturonase inhibitor | AL381114 | 1.80 | 1.00 | 1.89 | 0.97 | NS | 1.00 |
| TC86002 | PR1 | AL386306 | 1.00 | 1.00 | 5.22 | 1.63 | 2.81 | 1.00 |
| TC86646 | β-1,3-glucanase | AL378026 | 1.09 | 1.00 | NS | 1.00 | 5.44 | 1.36 |
| *Oxidative stress* | | | | | | | | |
| TC76384 | ascorbate peroxidase | AL367369 | 1.60 | 2.40 | 1.00 | 0.90 | 0.74 | NS |
| TC85974 | peroxidase | AL371851 | 1.05 | 1.46 | NS | 2.77 | 5.38 | 2.69 |
| TC76946 | superoxide dismutase | AL375556 | 2.49 | 3.12 | 1.00 | 1.40 | NS | 1.00 |
| TC86106 | glutathione peroxidase | AL374155 | 0.88 | 1.43 | 1.40 | NS | 2.08 | 1.90 |
| TC85451 | glutathione S-transferase | AL368847 | 1.00 | 1.16 | 1.00 | 1.15 | 1.55 | 3.01 |
| TC87485 | similar to a germin | AL373691 | NS | 1.32 | 1.10 | 1.16 | NS | NS |
| *Senescence-HR* | | | | | | | | |
| TC78195 | HSR203 | AL366024 | 1.34 | 2.58 | 4.38 | 1.98 | 2.78 | 1.31 |
| *Lipid signaling* | | | | | | | | |
| TC76357 | phospholipase D | AL383583, AL387293 | 1.60 | 1.39 | 1.44 | 2.75 | 5.49 | 2.40 |
| TC77257 | hydroperoxide lyase | AL372355 | 1.35 | 0.74 | 1.21 | 0.84 | 7.20 | 1.73 |
| TC82008 | phospholipase C | AL380498 | 1.00 | 1.04 | NS | 1.37 | 4.17 | 3.45 |
| TC84245 | lipoxygenase | AL371045, AL389771 | 1.00 | 1.14 | 1.46 | 1.57 | 1.86 | 0.83 |
| TC85148 | lipoxygenase | AL370268, AL381315 | 1.75 | NS | 1.11 | 2.04 | 2.03 | 1.03 |
| TC85171 | lipoxygenase | AL378899, AL380164 | 1.00 | NS | 1.53 | 2.27 | 2.75 | NS |
| TC85192 | lipoxygenase | AL387727 | 2.14 | 1.02 | 2.04 | 1.16 | NS | 1.00 |
| TC85264 | lipoxygenase | AL371045, AL389771 | 1.00 | 1.14 | 1.46 | 1.20 | 1.57 | 1.86 |
| TC85619 | lipoxygenase | | 1.00 | 1.93 | 2.05 | 1.44 | NS | 0.78 |
| TC85808 | oxophytodienoate reductase | | 1.00 | NS | 1.00 | 1.49 | 1.92 | 4.42 |
| TC85814 | desaturase | AL367066, AL377575 | 1.54 | 0.91 | 0.95 | 2.28 | 1.63 | 1.41 |
| *Abiotic stress* | | | | | | | | |
| TC77019 | ribonuclease | AL371802 | 1.52 | 2.72 | 1.67 | 0.47 | 0.80 | NS |
| *Signal transduction* | | | | | | | | |
| TC77346 | receptor-like protein kinase | AL383027, AL384392 | 1.66 | 1.44 | 4.89 | 1.28 | NS | 1.06 |
| TC76783 | calmodulin | AL378480 | 2.40 | 1.71 | 1.52 | 0.82 | 1.46 | NS |
| TC76643 | ABA response protein | AL373345 | 3.27 | 2.60 | 1.42 | 2.04 | 1.48 | NS |
| TC86374 | ABC transport protein | AL365693 | 1.44 | 1.98 | 2.71 | NS | 1.16 | NS |
| *Nodulin* | | | | | | | | |
| TC76916 | MtN4 | AL376203 | 0.89 | 1.11 | 1.14 | NS | 1.63 | 1.58 |
| *Others* | | | | | | | | |
| TC86776 | cyanogenic β-glucosidase | AL370555 | 1.03 | NS | 1.00 | 1.38 | 1.65 | 1.00 |
| TC78462 | nucleic acid-binding protein | AL367624 | 1.00 | NS | NS | NS | 3.41 | 3.30 |
| TC85305 | aquaporine | AL370135 | 1.04 | NS | NS | 2.02 | 1.93 | 2.61 |
| TC87062 | ubiquinol-cytochrome-c reductase | AL386789 | NS | 4.41 | 4.54 | 3.81 | 8.96 | NS |

[a] Values corresponding to the ratios of "intensities of the signals of the plants treated with the extract of *Ulva* (AV)" to the "intensities of the signals of the control plants". Only the genes inducted (ratio >1.5) in at least two independent experiments are included. When we compare the replicats of the three experiments, we can consider that the ratio of a single gene must not be induced in one replicat and repressed in at least one of the others, otherwise it is considered to be not significant (NS).
[b] TC TIGR, number of Tentative Consensus according to The Institute of Genome Research.
[c] GB, accession number in genebank.
[d] AV, a single AV treatment.
[e] AV + AV, two consecutive AV treatments.

EXAMPLE 3

Demonstration of the Effects of the Ulvans on the Plant Defense with Respect to Abiotic Stress The experiment is carried out on maize grown in pots at 25° C.

The extract of ulvans is applied via the roots or the leaves 17 days after seeding.

Four days after the treatment, the plants are subjected to a hydric or thermal (15° C.) stress.

The plants are harvested 21 days after the application of the stresses at the 8-leaf stage.

The results of this experiment are given in Table 4.

The use of ulvans makes it possible to partially combat the hydric and thermal stresses in response to the expression of the oxidative or abiotic stress genes.

TABLE 4

Effects of the ulvans on maize plants in a state of hydric or thermal stress

|  |  | Dry weight of the plant (as index) |
|---|---|---|
| Nonstressed control |  | 100 |
| *Hydric stress* | | |
| Control without ulvans |  | 60 |
| Application via the leaves | Ulvans 0.1 g/l | 82 |
| | Ulvans 10 g/l | 94 |
| Application via the roots | Ulvans 10 g/ha | 78 |
| | Ulvans 1000 g/ha | 89 |
| *Thermal stress* | | |
| Control without ulvans |  | 67 |
| Application via the leaves | Ulvans 1 g/l | 85 |
| | Ulvans 10 g/l | 99 |
| Application via the roots | Ulvans 10 g/ha | 84 |
| | Ulvans 1000 g/ha | 97 |

EXAMPLE 4

Demonstration of the Effects of Ulvans on the Plant Defense with Respect to Oomycetes The extract of ulvans is sprayed (1 g per liter, i.e. 200 g/ha) onto rapeseed plants grown in pots, at the 2-leaf stage.

The number of plantlets per treatment is 28. The inoculation with *Pythium* (damping off) is carried out 3 days after the treatment.

The plantlets are subjected to observation according to the following grading scale:

| | |
|---|---|
| 0 | No attack |
| 1 | Superficial necrosis less than 1 cm in length |
| 2 | Superficial necrosis greater than 1 cm in length |
| 3 | Deep necrosis less than 0.5 cm in length |
| 4 | Deep necrosis less than 1 cm in length |
| 5 | Deep necrosis greater than 1 cm in length |

The results obtained and given in Table 5 below show that the extract of ulvans according to the invention makes it possible to significantly reduce the effect of the *Pythium* attack, by reducing the length and the depth of the necroses.

TABLE 5

Effects of the treatment with ulvans on rapeseed infected with *Pythium*

|  | Control | Ulvans |
|---|---|---|
| Necrosis (index) | 2.92 | 1.61 |
| Fresh weight of plantlets (in g) | 0.49 | 0.69 |

The measurement of the fresh weight of the plantlets also confirms the better resistance of the rapeseed to fungal attack.

EXAMPLE 5

Demonstration of the Effects of the Ulvans on the Plant Defense with Respect with Other Fungal Attacks a) Alfalfa (*Medicago truncatula*)—*Colletotrichum trifolii* Interactions In order to verify whether the induction by the ulvans of the expression of the genes involved in defense is correlated with protection, an inoculation of the *Medicago truncatula* plants with the fungus *Colletotrichum trifolii* (responsible for anthracnose disease) is carried out on 1-month-old plants.

Two days after the final treatment with the extract of ulvans (1 g per liter), the plants are inoculated by spraying a concentrated suspension of *C. trifolii* spores at $10^6$ cells/ml, onto the parts above ground (1 ml/plant).

The first symptoms are observed 7 days and 15 days after infection.

One month later, the parts above ground are harvested and weighed so as to evaluate the degree of protection of the plant material.

Two weeks after inoculation, the parts above ground of the untreated plants are completely necrotic and most of the plants are dead. Conversely, only small lesions are visible on the leaves and stems in the case of the treatments (1 or 2 applications). The inoculated, untreated plants still alive lost 70% of their fresh weight in comparison with the noninoculated control plants. The plants inoculated and treated lost, for their part, respectively only 20% and 10% of their fresh weight for one or two applications.

A single treatment makes it possible to obtain a protection of 80%, while a second treatment brings the protection to 90%.

In accordance with genomic study, protection of the plants pretreated with the extract of ulvan is obtained. This protection is greater when the plants were treated twice consecutively with this extract before the infection.

b) Pea—*Mycosphaerella Pinodes* Interactions

The extract of ulvans (1 g per liter) is sprayed onto forage pea plants at the 4-leaf stage. The inoculation is carried out 3 days after the treatment.

The length of the necrosis resulting from the attack and also the fresh weight of the plantlet are measured.

The results obtained and represented in Table 6 below show that the extract of ulvans according to the invention reduces the length of the necroses on the stem.

There is a more than 25% increase in the fresh weight of the treated plantlets, which confirms the better resistance of the pea to the *Mycosphaerella* attack.

TABLE 6

Effects of the treatment with ulvans on
forage pea infected with *Mycosphaerella*

|  | Length of necrosis (mm) | Fresh weight of the plantlet (in g) |
| --- | --- | --- |
| Control | 3.17 | 2.75 |
| Ulvans | 1.79 | 3.45 | c) Pepper—*Phytophthora Capsicum* Interactions

Pepper plants cultivated in pots are watered with a solution of ulvans at a rate of 1 and 10 g per liter. The *Phytophthora* inoculation is carried out at the lower surface of the leaves 5 days after the treatment.

In the 3 days which follow the inoculation, a significant decrease in the size of the necroses is noted, as shown in Table 7 below.

TABLE 7

Evolution of the diameter of the necroses of
pepper plants after treatment with ulvans

|  |  | Ulvans | |
| --- | --- | --- | --- |
|  | Control | 1 g/l | 10 g/l |
| Diameter of the necroses (in mm) | 29 | 17 | 8 | d) Grapevine—*Plasmopara Viticola* Interactions

Grapevine plants cultivated in pots in a greenhouse are treated with a solution of ulvans (1 g per liter).

The treatment is carried out as 1 or 2 applications in the form of leaf spraying. The second application is carried out one week after the first treatment.

The inoculation with *Plasmopara viticola* is carried out 4 days after the final treatment.

One month after the contamination, the treatment with the solution of ulvans (one application) made it possible to reduce:

the ratio of infected leaves by 32%, the leaf surface affected by 35%, and the sporulation rate by 41%.

The double treatment improves these results with a 47% reduction in the percentage of infected leaves, a 46% reduction in the leaf surface affected and a 52% reduction in the sporulation rate.

EXAMPLE 6

Demonstration of the Effect of the Ulvans on the
Plant Defense with Respect to Bacterial Attacks An extract of ulvans according to the invention (1 g per liter) is sprayed onto tomato plants. Twenty-four hours later, the plants are inoculated with *Pseudomonas syringae*. The bacterial concentration of the leaves is determined 1, 3, 5 and 7 days after the inoculation, by counting the bacterial colonies.

The results obtained are reported in Table 8 below.

TABLE 8

Number of bacteria per unit of leaf surface area (no/cm$^2$)

|  | Time (days) | | | | |
| --- | --- | --- | --- | --- | --- |
| Treatment | 0 | 1 | 3 | 5 | 7 |
| Control | 18000 | 136000 | 385000 | 520000 | 636000 |
| Product | 24000 | 95000 | 224000 | 312000 | 440000 |

The treatment according to the invention makes it possible to reduce the level of contamination by close to 31% after incubation for 7 days.

EXAMPLE 7

Demonstration of the Effects of the Ulvans on the
Plant Defense with Respect to Insects and
Transmitted Pathogens (Viruses, Phytoplasms)

The experiment is carried out on rose bushes cultivated in pots in a greenhouse. The plants are treated with an extract of ulvans prepared according to Example 1 (0.1 g per liter or 10 g per liter) in comparison with a water control.

The number of aphids per leaf is then counted. The results obtained, represented in Table 9 below, show that the ulvans limit the aphid invasion in the treated plants, for all the treatments. At the concentration of 0.1 g per liter, the number of aphids is reduced by 35% in the case of the single treatment and by 42% in the case of the double treatment. At the concentration of 10 g per liter, the reduction in the mean number of aphids is 43% and 58%, respectively.

TABLE 9

Effect of the ulvan treatment on aphids

|  |  | Application via the leaves | Reduction in the number of aphids (as % of the control) |
| --- | --- | --- | --- |
| Ulvans | 0.1 g/l | 1 application | 35 |
|  |  | 2 applications | 42 |
|  | 10 g/l | 1 application | 43 |
|  |  | 2 applications | 58 |

EXAMPLE 8

Demonstration of the Effects of the Ulvans on the
Plant Defense with Respect to Acarids The trial is carried out on strawberry plants cultivated in a greenhouse, in a zone naturally sensitive to the development of acarids (*Tetranychus urticae*). The application of the extract of ulvans is carried out at two concentrations (0.1 and 10 g per liter) as a single application or as two applications one week apart.

The number of acarids per leaf is measured.

The results obtained, given in Table 10 below, show that the ulvans limit the acarid invasion in the treated plants, for all the treatments. At the concentration of 0.1 g per liter, the number of acarids is reduced by 33% in the case of the single treatment and by 46% in the case of the double treatment. At the concentration of 10 g per liter, the reduction in the mean number of acarids per leaf is 50% and 63%, respectively.

TABLE 10

Effect of the ulvan treatment on strawberry plants infected with acarids

|  |  | Application via the leaves | Number of acarids per leaf |
|---|---|---|---|
| Control (water) |  |  | 52 |
| Ulvans | 0.1 g/l | 1 application | 35 |
|  |  | 2 applications | 28 |
|  | 10 g/l | 1 application | 26 |
|  |  | 2 applications | 19 |

EXAMPLE 9

Demonstration of the Effects of the Ulvans on the Plant Defense with Respect to Nematodes Tomato plants approximately 10 cm in size are transplanted into a medium infested with *Meloidogyne incognita*.

The plants are treated either via the leaves or by incorporation into the ferti-irrigation nutritive medium, at the dose of 1 g per liter.

The second application of the treatment is carried out 15 days after the first application.

The number of nematodes is determined 1.5 months after the first treatment.

The results obtained were reported in Table 11

TABLE 11

Effect of the ulvan treatment on tomato plants infested with nematodes

|  |  | Number of nematodes/g of roots |
|---|---|---|
| Control |  | 15 |
| Application via the leaves | 1 application | 12 |
|  | 2 applications | 9 |
| Application by ferti-irrigation | 1 application | 10 |
|  | 2 applications | 7 |

The extract of ulvans significantly reduces the degree of infection of the roots of tomato plants with the nematodes by 20 to 53% according to the treatments.

A second application is always found to be more effective than a single application.

The extract of ulvans strengthens the plant's resistance to the nematodes by inhibiting the penetration and development of the latter in the root.

EXAMPLE 10

Demonstration of the Effects of the Ulvans on Seed Protection

It was demonstrated that the ulvans have a favorable action on the germination of seeds contaminated with pathogenic agents, just like *Sclerotinia* on sunflower, *Phoma linguam* on rapeseed and *Mycosphaerella pinodeson* pea.

The treatment of the seeds is carried out by soaking (for 12 hours in a solution of ulvans at 1 g per liter).

In the case of the control, the treatment is carried out with distilled water. The inoculation with the fungi is carried out just before sowing.

The percentage germination and the survival rate of the infected seeds were measured and the results obtained were grouped together in Table 12 below.

TABLE 12

Effects of the ulvans on seed protection

|  | Sunflower - *Sclerotinia* | | Rapeseed - *Phoma linguam* | | Pea - *Mycosphaerella* | |
|---|---|---|---|---|---|---|
|  | Control | Ulvans | Control | Ulvans | Control | Ulvans |
| % Germination | 38 | 80 | 63 | 88 | 67 | 89 |
| Survival rate (%) | 0 | 47 | 29 | 61 | 42 | 64 |

In sunflower, the inoculation with *Sclerotinia* greatly affects the germination rate (38%). The ulvan treatment considerably improves the germination rate (80%). It also strengthens the vigor of the plantlets, with a survival rate of 47% against complete mortality for the control.

In rapeseed infested with *P. linguam*, the ulvan treatment increases by 40% the germination rate, and also the survival rate, which goes from 29% for the control, to 61%.

In pea infested with *M. pinodes*, the ulvan treatment improves by 33% the germination rate, and also the survival rate, which goes from 42% to 64%.

In the case of pea, it was also observed that the depth of the necrosis goes from 52 mm to 2.9 mm, indicating a slowing down of the progression of the fungus in the plant.

The ulvans consequently induce a better resistance of the seeds to fungal attacks.

EXAMPLE 11

Demonstration of the Effects of the Ulvans on the Post-Harvest Protection of Fruits and Vegetables The effect of the ulvans on the conservation of fruits (apples, oranges, tomatoes and grapes) is followed in climatic chambers maintained at 17° C. The treatment by soaking is carried out with a solution of ulvans at the concentration of 10 g per liter.

The treated or control fruits are inoculated with a concentrated solution of *Botriytis cinerea* spores at $10^5$/ml. The inoculation is carried out one week after the treatment.

The fruits are controlled after 3 months for the apples and 1 month for the oranges, tomatoes and grapes.

The results obtained are given in Table 13 below.

TABLE 13

| Effect of the ulvans on the post-harvest protection of fruits and vegetables | |
|---|---|
| Fruits | Protection index (as % of inoculated control) |
| Apples | 65% |
| Oranges | 38% |
| Tomatoes | 42% |
| Grapes | 47% |

The ulvan treatment made it possible to reduce by 65%, 38%, 42% and 47%, respectively, the post-harvest damage for the apples, oranges, tomatoes and grapes.

The "ulvan" treatment prevents and delays the appearance of damage to the fruits during the storage thereof. It thus improves their storage time.

Consequently, the use of the ulvans according to the invention also makes it possible to reduce the post-harvest damage related to diseases or to attacks from pathogens.

EXAMPLE 12

Examples of Formulations Incorporating Ulvans

In general, the effective amount of ulvans or of ulvan-derived oligosaccharides to be used in the context of the uses of the invention will be from 0.1 to 100 g per liter, when applied in the form of a liquid via the leaves or in solutions for the roots (hydroponics, dropwise, etc.). Preferably, this amount will be from 0.1 to 20 g per liter, and more preferably from 0.5 to 10 g per liter.

In general, the effect amount of ulvans or of ulvan-derived oligosaccharides to be used in the context of the uses of the invention will be from 10 to 1000 g/ha when applied in the form of a solid in pulverulent or granulated products. Preferably, this amount will be from 50 to 500 g/ha, more preferably from 150 to 250 g/ha.

By way of examples, various formulations which can be used according to the invention will be given below, with indications regarding the conditions for using these formulations.

| A - ENRICHING AGENTS | |
|---|---|
| CALCAREOUS ENRICHING AGENT | |
| Lithothamnium | 1000 kg |
| Ulvan derivatives | QS 200 g/ha |
| Dose applied: 1 T/ha | |
| Calcium carbonate | 1000 kg |
| Ulvan derivatives | QS 1000 g/ha |
| Dose applied: 1 T/ha | |
| ORGANIC ENRICHING AGENT AND CROP SUPPORTS | |
| Compost | 500 kg |
| Peat | 500 kg |
| Ulvan derivatives | QS 500 g/ha |
| Dose applied: 1 T/ha | |

| B - ROOT FERTILIZERS | |
|---|---|
| NP FERTILIZER | |
| Lithothamnium | 310 kg |
| Potassium chloride | 167 kg |
| Urea | 161 kg |
| Aqueous ammonia sulfate | 362 kg |
| Ulvan derivatives | QS 200 g/ha |
| CROPS | DOSE APPLIED (kg/ha) |
| Pasture Cereals Maize | 200-400 |
| PK FERTILIZER | |
| Lithothamnium | 297 kg |
| Natural phosphate | 536 kg |
| Potassium chloride | 167 kg |
| Ulvan derivatives | QS 500 g/ha |
| CROPS | DOSE APPLIED (kg/ha) |
| All crops | 300-500 |
| NPK FERTILIZER + MgO | |
| Lithothamnium | 158 kg |
| Aqueous ammonia phosphate | 116 kg |
| Aqueous ammonia sulfate | 186 kg |
| Urea | 156 kg |
| Magnesium oxide | 50 kg |
| Potassium chloride | 334 kg |
| Ulvan derivatives | QS 1000 g/ha |
| CROPS | DOSE APPLIED (kg/ha) |
| Maize Cereals Grassland All crops | 400-800 |

| C - LEAF FERTILIZERS | | |
|---|---|---|
| Mg SOLUTION | | |
| Magnesium nitrate | | 50 kg |
| Water | | 50 kg |
| Ulvan derivatives | | QS 1 g/l (final solution applied to the plant) |
| CROPS | Number of applications at various stages of the campaign | Dose per application |
| Orchards | 3-6 | 8 l/ha |
| Market garden crops | 2-6 | 5-8 l/ha |
| N Fe Mn SOLUTION | | |
| Manganese nitrate | | 15 kg |
| Ferric chloride | | 25 kg |
| Water | | 60 kg |
| Ulvan derivatives | | QS 0.1 g/l (final solution applied to the plant) |
| CROPS | Number of treatments | Dose per treatment |
| Orchards | 4-6 | 3-6 l/ha |
| Market garden crops | 4-6 | 3-6 l/ha |

C - LEAF FERTILIZERS

N Mn Zn SOLUTION

| | |
|---|---|
| Manganese nitrate | 31 kg |
| Zinc nitrate | 22 kg |
| Water | 47 kg |
| Ulvan derivatives | QS 10 g/l (final solution applied to the plant) |

| CROPS | Number of applications | Dose per application |
|---|---|---|
| Maize | 1-2 | 4-8 l/ha |
| Flax | 1-2 | 4-8 l/ha |
| Beetroot | 1-3 | 4-8 l/ha |
| Soybean | 1-2 | 4-8 l/ha |
| Potato | 1-3 | 4-8 l/ha |
| Pea beans | 2-3 | 4-8 l/ha |

NPK Trace elements SOLUTION

| | |
|---|---|
| Urea | 17 kg |
| Phosphoric acid | 9 kg |
| Potassium hydroxide | 9 kg |
| Manganese nitrate | 0.7 kg |
| Zinc nitrate | 0.3 kg |
| Copper nitrate | 0.10 kg |
| Ferric chloride | 0.20 kg |
| Boric acid | 0.4 kg |
| Water | 63.3 kg |
| Ulvan derivatives | QS 1 g/l (final solution applied to the plant) |

| CROPS | Number of applications | Dose per application |
|---|---|---|
| Market garden crops | 5-10 | 4-6 l/ha |
| Orchards | 4-6 | 4-6 l/ha |

BPK SOLUTION

| | |
|---|---|
| Potassium hydroxide | 8 kg |
| Phosphoric acid | 1 kg |
| Boric acid | 1 kg |
| Water | 90 kg |
| Ulvan derivatives | QS 10 g/l (final solution applied to the plant) |

| CROPS | Number of applications | Dose per application |
|---|---|---|
| Market garden crops | 2-4 | 3-5 l/ha |
| Fruit crops | 3 | 5 l/ha |

D - NUTRITIVE SOLUTIONS FOR THE ROOTS (HYDROPONICS, DROPWISE)

NPK Mg SOLUTION

| | |
|---|---|
| Potassium nitrate | 50 g/l |
| Potassium phosphate | 27 g/l |
| Magnesium sulfate | 49 g/l |
| Ulvan derivatives | 200 g/l (i.e. 1 g/l of final solution applied to the plant) |
| Dilution 1 l per 200 l of water | |

N Ca Mg SOLUTION

| | |
|---|---|
| Calcium nitrate | 118 g/l |
| Iron chelate | 5 g/l |
| Ulvan derivatives | 100 g/l (i.e. 0.5 g/l of final solution applied to the plant) |
| Dilution 1 l per 200 l of water | |

The invention claimed is:

1. A method for activating, in vivo, plant defense and resistance reactions against biotic or abiotic stresses comprising administering to living plants or seeds a composition that has an effective concentration of ulvans extracted from green algae of the genus *Ulva* or *Enteromorpha*, wherein administering to the living plants or the seeds is effected under in vivo conditions.

2. The method as claimed in claim 1, wherein the administering to the living plants is carried out via leaves or via roots of the living plants.

3. The method as claimed in claim 1, wherein the composition is a solution, and the effective concentration of the ulvans is from 0.1 g to 100 g per liter of the solution.

4. The method as claimed in claim 1, wherein the effective concentration of ulvans is from 10 to 1000 g per hectare.

5. The method as claimed in claim 4, wherein the effective concentration of ulvans is 200 g per hectare.

6. A method for activating, in vivo, plant defense and resistance reactions against biotic stresses comprising administering to living plants or seeds an effective amount of a composition comprising ulvans extracted from green algae of the genus *Ulva* or *Enteromorpha*, wherein administering to the living plants or the seeds is effected under in vivo conditions.

7. The method as claimed in claim 3, wherein the effective concentration of the ulvans is 1 g per liter of the solution.

8. The method as claimed in claim 3, wherein the administering of the composition is to (1) leaves or roots of the living plants or (2) post harvest treatment of the living plants.

9. The method as claimed in claim 8, wherein the administering of the composition is to the roots of the living plants and the solution is a nutritive solution.

10. The method as claimed in claim 9, wherein the nutritive solution is administered dropwise to the roots to provide the nutritive solution to the roots.

11. The method as claimed in claim 9, wherein the nutritive solution is administered to the roots in a hydroponics system.

12. The method as claimed in claim 1, wherein the administering of the composition is to the seeds.

13. The method as claimed in claim 12, wherein the composition is a solution, and the effective concentration of the ulvans is from 0.1 g to 100 g per liter of the solution.

14. The method as claimed in claim 1, wherein the administering is in the form of a solid, and the solid is in a powdered form or a granulated form.

* * * * *